United States Patent [19]

Taylor

[11] Patent Number: Plant 6,471

[45] Date of Patent: Dec. 20, 1988

[54] NECTARINE

[75] Inventor: James W. Taylor, Dinuba, Calif.

[73] Assignee: Ito Packing, Inc., Reedley, Calif.

[21] Appl. No.: 939,873

[22] Filed: Dec. 9, 1986

[51] Int. Cl.[4] ..... A01H 5/03
[52] U.S. Cl. ..... Plt./41
[58] Field of Search ..... Plt./41

*Primary Examiner*—Robert E. Bagwill
*Attorney, Agent, or Firm*—Dennis B. Haase

[57] ABSTRACT

A new and distinct variety of nectarine distinguished by its yellow fleshed fruit and deep red coloring which, together with its round shape, depressed apex and firm flesh make the fruit particularly resistant to bruising.

1 Drawing Sheet

BACKGROUND OF THE VARIETY

The present invention relates to a new and distinct variety of nectarine tree which I refer to as Diamond Jim, and which comprises a yellow fleshed, clingstone fruit, attractive in appearance in the early season, which was developed from a continued fruit breeding program.

ORIGIN AND ASEXUAL REPRODUCTION OF THE NEW VARIETY

This invention was derived from an ongoing fruit breeding program started at Le Grand, Calif. where I was plant breeder and program manager for Mr. Fredric W. Anderson of Merced, Calif. The variety Regal Grand (U.S. Plant Pat. No. 1,751) resulted from this program and produced a mutation in the orchard of James Sorensen subsequently called Red Jim (U.S. Plant Pat. No. 4,518). Flowers from the Red Jim variety were emasculated and pollinated with pollen from the May Glow variety (U.S. Plant Pat. No. 5,245). Seed produced with this method were stratified and grown to a height of about 18 inches. These seedlings were bud grafted into dehorned orchard trees in the experimental orchard of Ito Packing Co., Inc., Reedley, Calif., for testing and selection. Each clone was budded into several limbs to make sure that it propagated true to type.

SUMMARY OF THE NEW VARIETY

The instant variety developed through the above method was selected because of its unique bright red color at harvest maturity. This bright color is found even in fruit growing under the foliage where little light penetrates. The fruit is very large in size and the flesh is firm so as to resist bruising often encountered in harvesting and commercial packing. Furthermore, the fruit has an exceptionally fine eating quality with approximately 14% soluble solids (taken by refractometer) at harvest maturity which increases to about 16% at eating maturity.

The flowering season begins approximately 10 days ahead of the variety Red Jim and a few days later than that of May Glow. The fruit matures about 3 to 4 days ahead of the variety May Grand (U.S Plant Pat. No. 2,794). It is differentiated from this variety by being of larger size, a darker red color, rounder in shape and a more recessed ventral suture and slightly more depressed pistol point.

BRIEF DESCRIPTION OF THE DRAWING

The accompanying drawing illustrates typical specimens of the fruit and foliage of my new variety, as grown in the San Joaquin Valley of California. One specimen is shown in an elevation showing one of the fruit of the present variety with twig and leaves; one other specimen is a sectional elevation of one of the fruit with the stone exposed.

DETAILED DESCRIPTION

The following is a detailed description of my new variety with color reference being to the Maerz and Paul Dictionary of Colors, except in instances where terminology having generally accepted meaning is employed.

Parentage: Red Jim and May Glow (F1).
Propagation: Maintains its distinguishing characteristics through succeeding asexual propagations.
Locality where grown and observed: Near Reedley, County of Fresno, Calif.

TREE

Size: Large, spreading, open, vase form.
Vigor: Vigorous; very productive.
Regularity of bearing: A regular bearer.
Trunk: Medium.
Branches: Strong growth with average stockiness.
Leaves:
- *Color.*—Top side medium green 22L7; underside lighter green 22H4.
- *Size.*—Average $5\frac{3}{4}$ inches in length and $1\frac{2}{3}$ inches in width; medium thickness.
- *Shape.*—Lancelate.
- *Marginal form.*—Glandular; crenate.
- *Glandular characteristics.*—Reniform; usually one on either side near the base of the leaf but may be on petiole.
- *Petiole.*—Medium in length and thickness.
- *Stipules.*—Small in early stages and then disappearing with maturity.

Flower bud: Large, showy, pink.
Flower: Large, showy, pink.
- *Anthers.*—Red.

FRUIT

Maturity: When described hard ripe, May 28, 1986. First picking date May 28 and last picking date June 10, 1986.

Size: Large; Average in axial diameter $2\frac{5}{8}''$; Average Size in Suture Plane, $2\frac{5}{8}''$.

*Uniformity.*—Generally large and uniform.

*Axial diameter.*—$2\frac{5}{8}$ inches in the plane of the suture.

*Transverse diameter.*—$2\frac{5}{8}''$.

*Transverse diameter at right angles to suture plane.*—$2\frac{5}{8}''$.

Form: Mostly uniform in shape, symmetrical and nearly round.

*Tendency to split.*—Seldom.

*Tendency to crack.*—None.

*Base.*—Round.

*Apex.*—Rounded, slightly recessed at suture.

*Suture.*—Distinct; shallow; extends from the base to beyond the apex; pistol point lies in recessed area between lips.

Stem: Elongated in suture plane; depth of $\frac{1}{2}$ inch; breadth of $\frac{3}{4}$ inch.

Skin:

*Thickness.*—Medium thick; medium texture.

*Color.*—Brown (7L12) shaded to reddish purple (47L1) through.

*Suture stripe.*—None — only important in mutations.

Flesh:

*Texture.*—Firm, meaty.

*Color.*—Yellow (9L1) with red (5L7) interspersed throughout, but more intense at ventral suture and around pit.

*Juice.*—Abundant, rich.

*Flavor.*—Mildly acid and sweet.

*Aroma.*—Not very pronounced.

*Fibers.*—Few.

*Ripening.*—Even, stays firm for long period.

*Eating quality.*—Excellent.

Stone:

*Adherence to flesh.*—Cling.

*Size.*—Average thickness 11/16"; Average width 1-1/16"; Average length $1\frac{3}{8}''$.

*Form.*—Oval.

*Hilum.*—Small, oblong.

*Dorsal edge.*—Shallow grooves; oval in suture plane.

*Ventral edge.*—Interrupted by furrows; ventral grooves shallow; wings discontinuous about $\frac{1}{4}''$ in from apex in some stones.

*Surface.*—Irregular short furrows toward the base; irregularly pitted throughout;

*Color.*—Brown (7L12) shaded to reddish purple (47L1) throughout.

Use: Shipping.

Keeping quality: Excellent.

Shipping quality: Excellent.

Resistance to disease: Similar to other reniform vigorous nectarine varieties.

Although the new variety of nectarine tree possesses the described characteristics as a result of the growing conditions in Fresno County, Calif., in the central portion of the San Joaquin Valley, it is to be understood that variations of the usual magnitude in characteristics incident to growing conditions, fertilization, pruning and pest control are to be expected.

Having thus described and illustrated my new variety of nectarine tree, what is claimed as new and desired to be secured by letters Patent is:

1. A new and distinct variety of nectarine tree with fruit of the yellow fleshed cling type, substantially as herein shown and described, particularly as to the novelty of the deep red coloring of the fruit with a very waxy surface that produces a brilliant deep red color at commercial harvest time, with good sugar content and well balanced acid content resulting in an excellent flavor, and further having a round shape and depressed apex along with very firm flesh making the fruit particularly resistant to bruising; furthermore, the round shape and depressed apex along with the very firm flesh make the fruit very resistant to bruising.

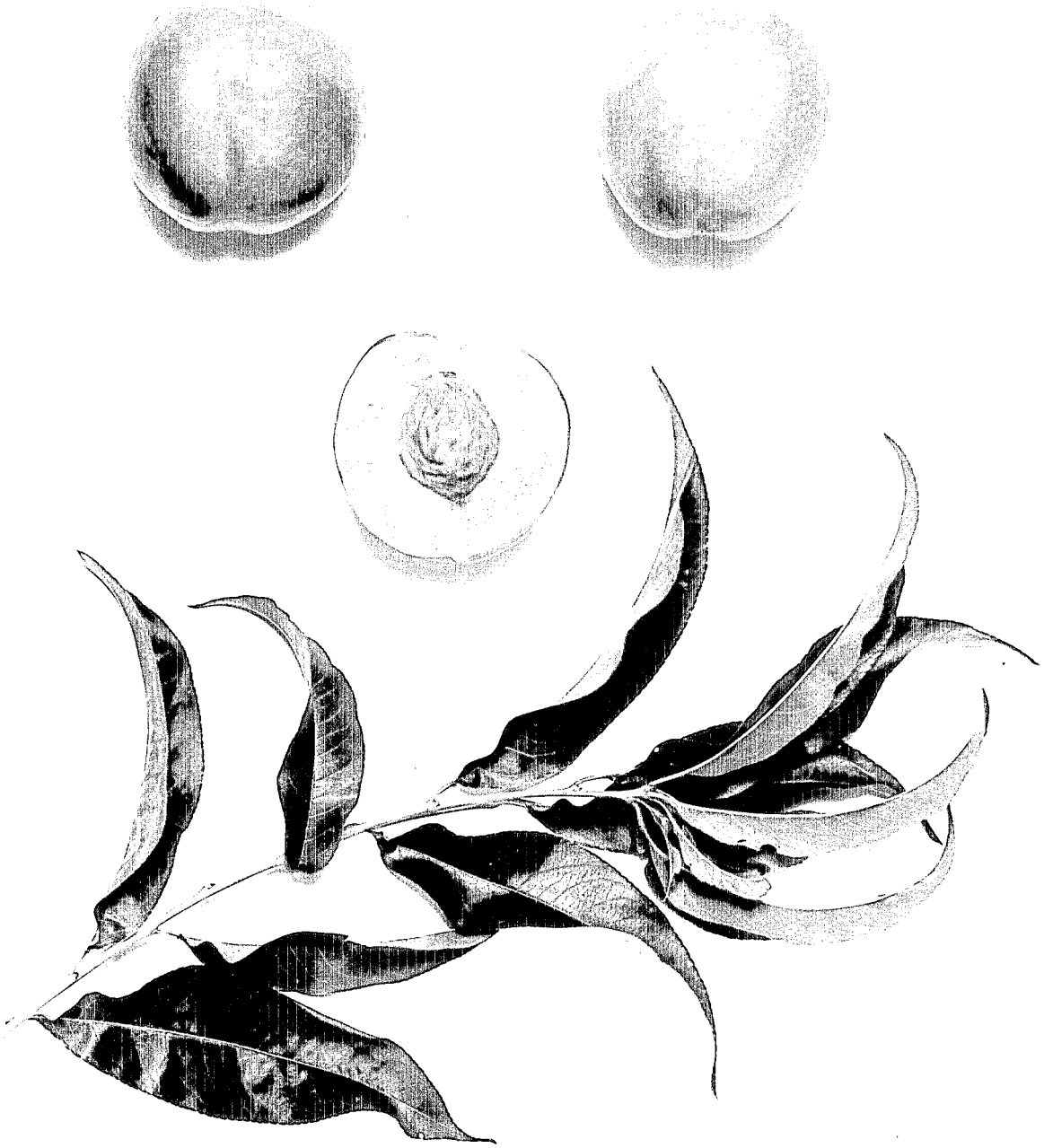

* * * * *